US011793932B2

(12) United States Patent
Lee (10) Patent No.: US 11,793,932 B2
(45) Date of Patent: *Oct. 24, 2023

(54) MEDICINE INJECTION DEVICE (71) Applicant: IMPACT KOREA CO., LTD., Anyang-si (KR)

(72) Inventor: Moung Sook Lee, Anyang-si (KR)

(73) Assignee: IMPACT KOREA CO., LTD., Anyang-si (KR)

( * ) Notice: Subject to any disclaimer, the term of this patent is extended or adjusted under 35 U.S.C. 154(b) by 801 days.

This patent is subject to a terminal disclaimer.

(21) Appl. No.: 16/765,548

(22) PCT Filed: Nov. 13, 2018

(86) PCT No.: PCT/KR2018/013814
§ 371 (c)(1),
(2) Date: Jul. 14, 2020

(87) PCT Pub. No.: WO2019/103386
PCT Pub. Date: May 31, 2019

(65) Prior Publication Data
US 2022/0409807 A1   Dec. 29, 2022

(30) Foreign Application Priority Data
Nov. 21, 2017   (KR) .......................... 10-2017-0155538

(51) Int. Cl.
*A61M 5/148*   (2006.01)
*A61M 5/168*   (2006.01)
*A61M 5/44*    (2006.01)

(52) U.S. Cl.
CPC ...... *A61M 5/1486* (2013.01); *A61M 5/16881* (2013.01); *A61M 5/44* (2013.01); *A61M 2205/368* (2013.01)

(58) Field of Classification Search
CPC ........ A61M 2205/3331; A61M 5/1483; A61M 5/1486; A61M 5/152; A61M 5/155; A61M 5/148; A61M 2205/368; A61M 5/44
See application file for complete search history.

(56) References Cited

U.S. PATENT DOCUMENTS 6,306,113 B1 * 10/2001 Beyersdorf ......... A61M 1/3613
                                                  604/407
11,400,237 B2 * 8/2022 Lee .................... A61M 5/16813
(Continued)

FOREIGN PATENT DOCUMENTS

JP   2006-051281 A   2/2006
JP   2010-099406 A   5/2010
(Continued)

*Primary Examiner* — Quynh-Nhu H. Vu
(74) *Attorney, Agent, or Firm* — KORUS Patent, LLC; Seong Il Jeong (57) ABSTRACT Provided is a medicine injection device capable of injecting a liquid medicine into a human body by using a medicine container configured to discharge the medicine contained therein along a designated path when a pressure is applied from outside, the medicine injection device including one or more medicine pressing units including one or more inflatable parts capable of being inflated by air to apply a pressure to the medicine container, and a first pumping unit capable of inflating one of the inflatable parts by including a first pump capable of generating air of a preset pressure, and a first pipe connectable to the one of the inflatable parts. According to the present invention, a risk of breakdown and a total manufacturing cost may be reduced due to a simple structure of the medicine injection device.

6 Claims, 7 Drawing Sheets (56) References Cited

U.S. PATENT DOCUMENTS

2009/0043256 A1\* 2/2009 Landy .................. A61M 1/166
                                                                604/113
2017/0165409 A1\* 6/2017 Li .......................... A61M 1/77

FOREIGN PATENT DOCUMENTS

JP       2017-018781 A    1/2017
KR   10-2016-0122723 A   10/2016

\* cited by examiner

MEDICINE INJECTION DEVICE

TECHNICAL FIELD

The present invention relates to a medicine injection device, and more particularly, to a medicine injection device having a simple structure to reduce a risk of breakdown and a total manufacturing cost.

BACKGROUND ART

A fluid is a sort of medical solution to be injected into a human body to treat a shock, dehydration, malnutrition, or the like, and includes blood and various electrolyte solutions which are isotonic with blood, e.g., a physiological saline and a Ringer's solution.

Figure 3:
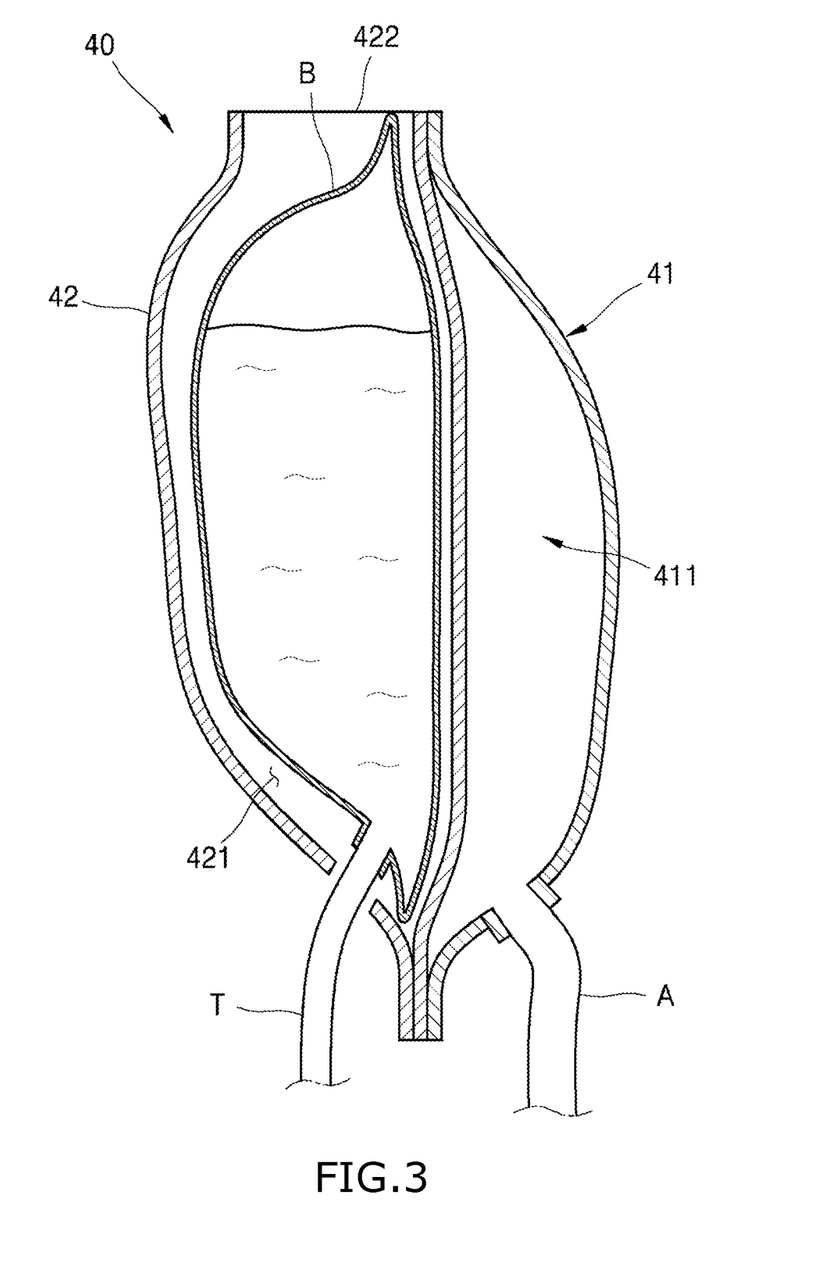
FIG. 3 is a vertical cross-sectional view of a medicine pressing unit illustrated in FIG. 1.

In general, a fluid bag such as a medicine container B illustrated in FIG. 3 is hanged upside down above a human body and a medicine is injected into the human body through a tube T and a needle N connected to the medicine container B.

However, although a large amount of medicine needs to be rapidly injected into, for example, a surgical patient at an accurate flow rate with an accurate dose, the general medicine injection device may not easily achieve this goal.

Medicine injection devices such as piston-type and syringe-type medicine injection devices have been developed to solve the above problem, but have high risks of breakdown and high total manufacturing costs due to complicated structures thereof.

DETAILED DESCRIPTION OF THE INVENTION

Technical Problem

The present invention provides a medicine injection device having a simple structure to reduce a risk of breakdown and a total manufacturing cost.

Technical Solution

According to an aspect of the present invention, there is provided a medicine injection device capable of injecting a liquid medicine into a human body by using a medicine container configured to discharge the medicine contained therein along a designated path when a pressure is applied from outside, the medicine injection device including one or more medicine pressing units including one or more inflatable parts capable of being inflated by air to apply a pressure to the medicine container, and a first pumping unit capable of inflating one of the inflatable parts by including a first pump capable of generating air of a preset pressure, and a first pipe connectable to the one of the inflatable parts.

The medicine injection device may further include a second pumping unit capable of inflating one of the inflatable parts by including a second pump capable of generating air of a preset pressure, and a second pipe connectable to the one of the inflatable parts.

The medicine injection device may further include a connection unit including a connection pipe for interconnecting the first and second pipes, and a connection pipe valve capable of opening or closing the connection pipe, and one or more inflatable parts connected to the first and second pipes may be inflated by operating one of the first and second pumps when another of the first and second pumps does not operate.

The medicine injection device may further include a first upstream valve provided at an upstream side of the first pipe, a first downstream valve provided at a downstream side of the first pipe, a second upstream valve provided at an upstream side of the second pipe, and a second downstream valve provided at a downstream side of the second pipe, and the connection pipe may have one end connected to the first pipe between the first upstream valve and the first downstream valve, and another end connected to the second pipe between the second upstream valve and the second downstream valve.

The medicine injection device may further include a heating unit for heating the medicine discharged from the medicine container, within a preset temperature range.

The heating unit may include a magnetic field generator for generating a magnetic field, and a heater heated by a current induced by the magnetic field, to operate based on induction heating (IH).

The heater may be configured to surround a tube which is connected to the medicine container and in which the medicine flows.

The medicine container may have a shape of a flexible bag.

Advantageous Effects of the Invention

According to the present invention, a medicine injection device capable of injecting a liquid medicine into a human body by using a medicine container configured to discharge the medicine contained therein along a designated path when a pressure is applied from outside includes one or more medicine pressing units including one or more inflatable parts capable of being inflated by air to apply a pressure to the medicine container, and a first pumping unit capable of inflating one of the inflatable parts by including a first pump capable of generating air of a preset pressure, and a first pipe connectable to the one of the inflatable parts, and thus may reduce a risk of breakdown and a total manufacturing cost due to a simple structure thereof.

BEST MODE

Hereinafter, the present invention will be described in detail by explaining embodiments of the invention with reference to the attached drawings.

Figure 1:
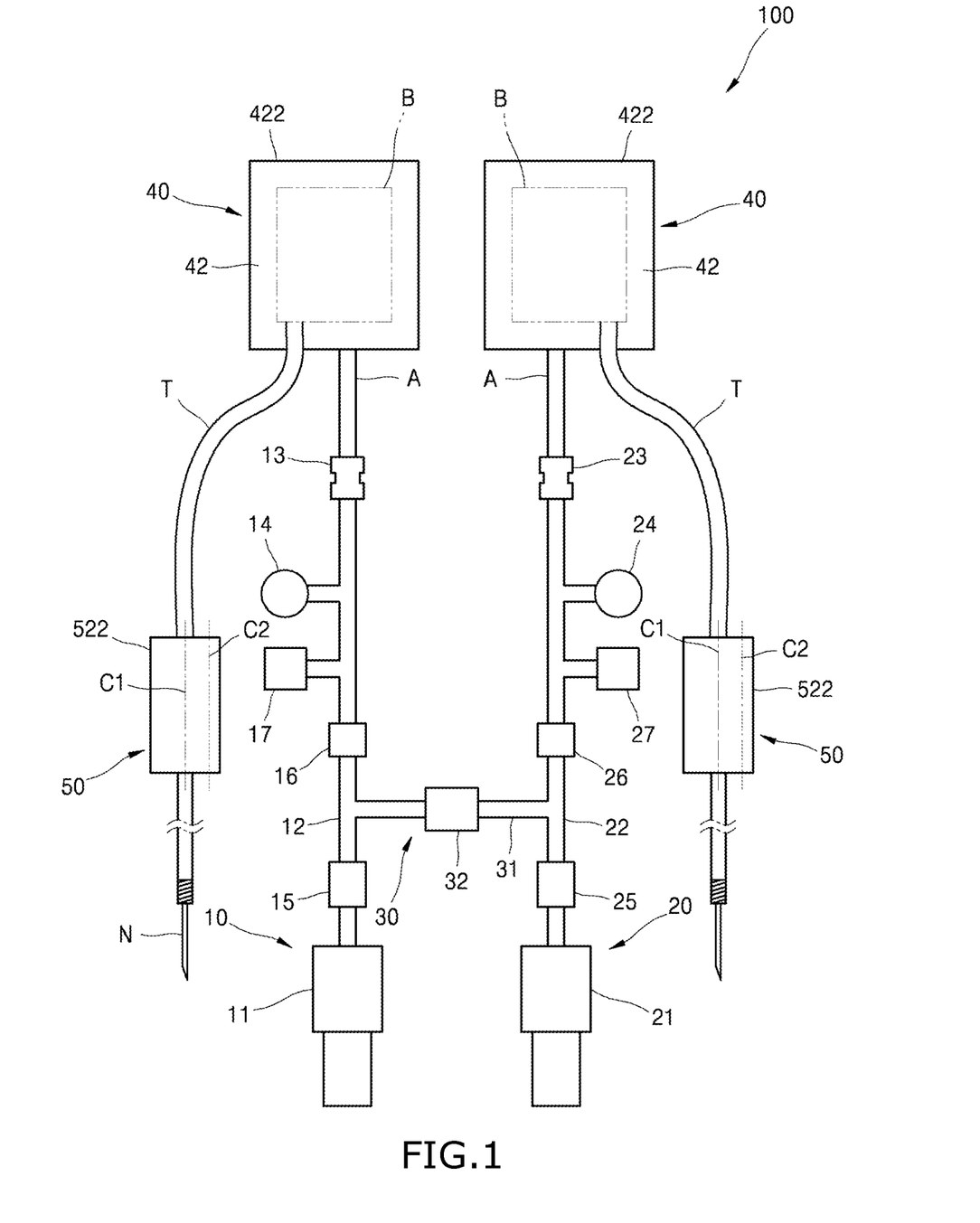
FIG. 1 is a front view of a medicine injection device according to an embodiment of the present invention.
Figure 2:
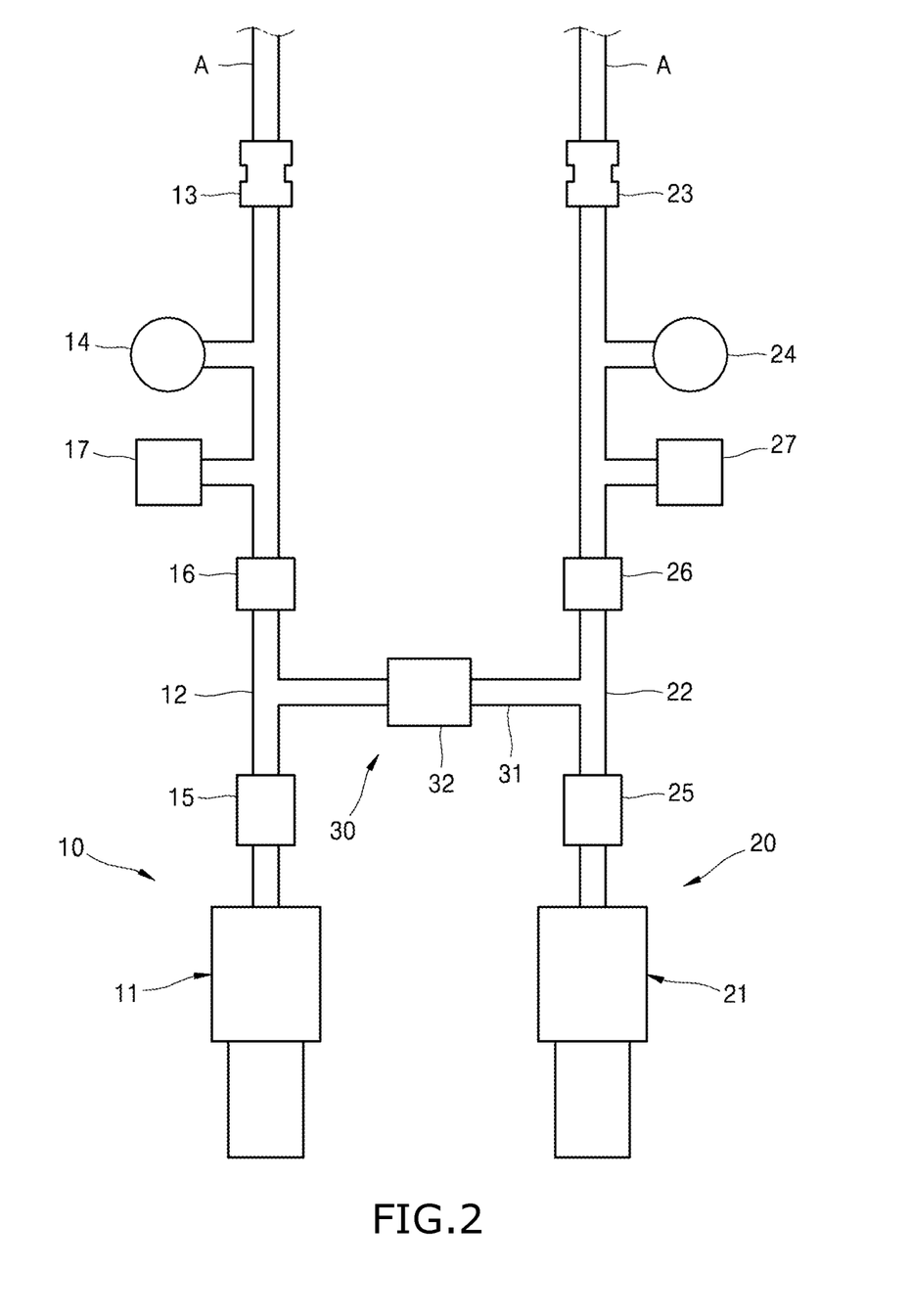
FIG. 2 is a front view of a first pumping unit and a second pumping unit illustrated in FIG. 1.

FIG. 1 is a front view of a medicine injection device 100 according to an embodiment of the present invention, and FIG. 2 is a front view of a first pumping unit 10 and a second pumping unit 20 illustrated in FIG. 1. FIG. 3 is a vertical cross-sectional view of a medicine pressing unit 40 illustrated in FIG. 1.

Referring to FIGS. 1 to 3, the medicine injection device 100 according to an embodiment of the present invention is a medicine injection device capable of injecting a liquid medicine such as a fluid into a human body, uses medicine containers B each configured to discharge the liquid medicine contained therein along a designated path when a pressure is applied from outside, and includes the first pumping unit 10, the second pumping unit 20, a connection unit 30, the medicine pressing units 40, and heating units 50. The following description assumes that the medicine containers B have a shape of a flexible synthetic resin bag. In this case, the medicine container B are generally produced in a shape of a transparent or translucent bag by using synthetic resin such as polyvinyl chloride, polybutadiene, or polystyrene.

The first pumping unit 10 is an apparatus capable of inflating an inflatable part 41 of the medicine pressing unit 40, and includes a first pump 11, a first pipe 12, and a first outlet 13.

The first pump 11 is an air pump operating by electricity, and may generate air of a preset pressure.

The first pipe 12 is a pipe having one end connected to the first pump 11 and the other end connectable to the inflatable part 41.

In the current embodiment, the first pipe 12 includes a circular synthetic resin tube.

The first outlet 13 is provided at the other end of the first pipe 12, and is a hole for discharging the air supplied from the first pump 11.

The first outlet 13 is connected to an air tube A connected to the inflatable part 41.

At an upstream side of the first outlet 13, a first sensor 14 capable of measuring an internal air pressure of the first pipe 12 is mounted as illustrated in FIG. 1.

At an upstream side of the first sensor 14, a first exhaust valve 17 for discharging air stored in an internal space 411 of the inflatable part 41, to outside in an emergency, e.g., a case when an internal air pressure of the inflatable part 41 is excessively high or a case when the first pump 11 operates over a set time, is mounted.

In the current embodiment, the first exhaust valve 17 includes a 1-way solenoid valve operating by electricity, and is normally closed.

At an upstream side of the first exhaust valve 17, a first downstream valve 16 capable of opening or closing the first pipe 12 to or not to allow the air to flow in the first pipe 12 is mounted.

In the current embodiment, the first downstream valve 16 includes a 2-way solenoid valve operating by electricity.

When the first downstream valve 16 is closed, the pressed air may not flow into the inflatable part 41 and the air in the inflatable part 41 may not flow backward into the first pump 11.

At an upstream side of the first downstream valve 16, a first upstream valve 15 capable of opening or closing the first pipe 12 to or not to allow the air to flow in the first pipe 12 is mounted.

In the current embodiment, the first upstream valve 15 includes a 2-way solenoid valve operating by electricity.

When the first upstream valve 15 is closed, the pressed air generated from the first pump 11 may not flow toward the first downstream valve 16 and the air in the first pipe 12 connected to a connection pipe 31 may not flow backward into the first pump 11.

Like the first pumping unit 10, the second pumping unit 20 is an apparatus capable of inflating the inflatable part 41 of the medicine pressing unit 40, and includes a second pump 21, a second pipe 22, a second outlet 23, a second sensor 24, a second upstream valve 25, a second downstream valve 26, and a second exhaust valve 27.

In the current embodiment, the second pump 21, the second pipe 22, the second outlet 23, the second sensor 24, the second upstream valve 25, the second downstream valve 26, and the second exhaust valve 27 of the second pumping unit 20 are the same as or correspond to the first pump 11, the first pipe 12, the first outlet 13, the first sensor 14, the first upstream valve 15, the first downstream valve 16, and the first exhaust valve 17 of the first pumping unit 10, respectively, and thus detailed descriptions thereof are not provided herein.

The connection unit 30 is an apparatus for interconnecting the first and second pipes 12 and 22, and includes the connection pipe 31 and a connection pipe valve 32.

The connection pipe 31 is a pipe for interconnecting the first and second pipes 12 and 22, and has one end connected to the first pipe 12 between the first upstream valve 15 and the first downstream valve 16 of the first pipe 12, and the other end connected to the second pipe 22 between the second upstream valve 25 and the second downstream valve 26 of the second pipe 22.

The connection pipe valve 32 is a valve capable of opening or closing the connection pipe 31 to or not to allow the air to flow in the connection pipe 31.

In the current embodiment, the connection pipe valve 32 includes a 2-way solenoid valve operating by electricity.

The medicine pressing unit 40 is an apparatus capable of pressing the medicine container B, and a pair of the medicine pressing units 40 are separately connected to the first and second pumping units 10 and 20. Each of the medicine pressing units 40 includes the inflatable part 41 and a medicine container holder 42.

The inflatable part 41 is an inflatable part having a sealable internal space 411, and is configured to inflate as illustrated in FIG. 3 when the air is injected into the internal space 411.

The internal space 411 of the inflatable part 41 is connected to each of the first and second outlets 13 and 23 by the air tube A as illustrated in FIGS. 1 and 3.

In the current embodiment, the inflatable part 41 has a shape of a rectangular bag produced by combining two sheets of synthetic resin film, but may also have a shape of an arbitrary bag, e.g., a shape of a circular or polygonal bag.

In the current embodiment, a pressure of the inflatable part 41 may be adjusted to a value desired by a user, e.g., 100 mmHg, 200 mmHg, or 300 mmHg.

The inflatable part 41 is configured to apply a pressure to the medicine container B when the air is injected into the internal space 411.

The inflatable part 41 may be made of a material that does not easily burst when inflated.

The medicine container holder 42 is a part having an internal space 421 capable of accommodating the medicine container B.

The medicine container holder 42 is in contact with a bottom surface of the inflatable part 41 as illustrated in FIG. 3.

At one end of the medicine container holder 42, a medicine container slot 422 for inserting or taking the medicine container B into or out of the internal space 421 is provided.

The medicine container holder 42 may have a material and a thickness not to be easily stretchable when the inflatable part 41 inflates to press the medicine container B. When the medicine container holder 42 is made of an easily stretchable material, although the inflatable part 41 inflates, the medicine container B may not be sufficiently pressed.

Figure 4:
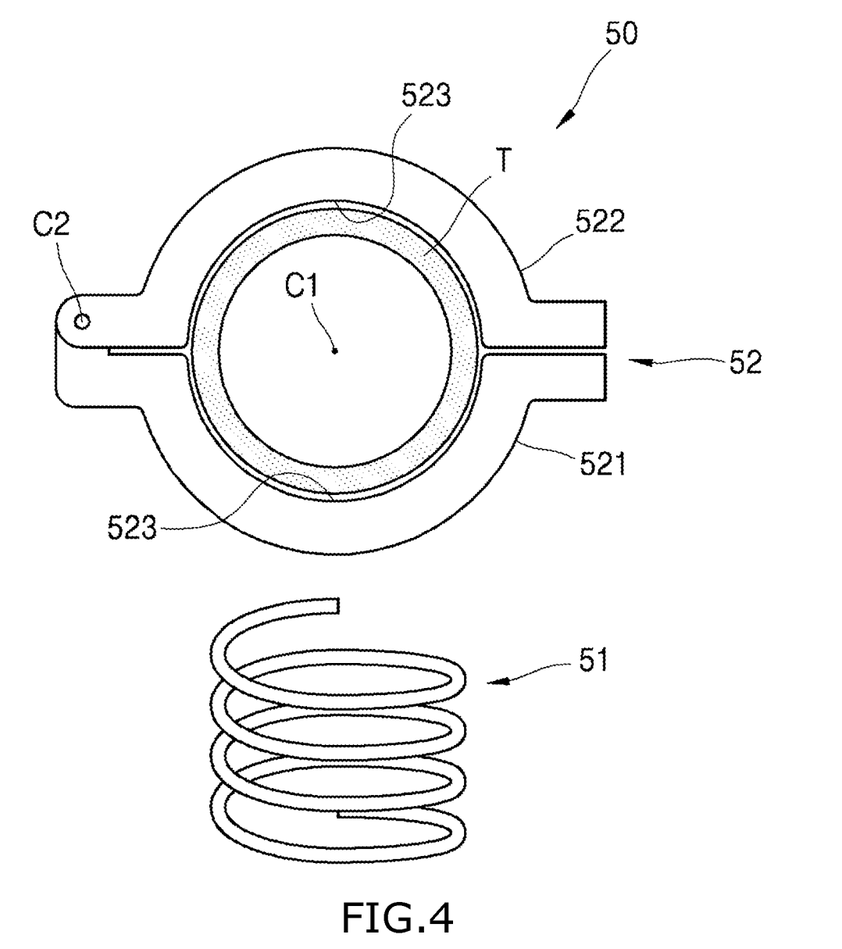
FIG. 4 is a top view of a heating unit illustrated in FIG. 1.

Each of the heating units 50 is an apparatus for heating the medicine discharged from the medicine container B, within a preset temperature range, operates based on induction heating (IH), and includes a magnetic field generator 51 and a heater 52 as illustrated in FIG. 4.

The magnetic field generator 51 is a part for generating a magnetic field near the heater 52, and may include a coil through which electricity flows.

The heater 52 is a part including a metal heated by a current induced by the magnetic field generated by the magnetic field generator 51, and includes a heater body 521, a heater cover 522, and tube accommodating grooves 523.

The heater body 521 is a member extending along a first central axis C1 as illustrated in FIGS. 1 and 4, and includes a semicircular tube accommodating groove 523 configured to surround and accommodate a lower part of a circular tube T.

The tube T is a circular tube in which the medicine flows, and has one end connected to the medicine container B and the other end connected to a needle N insertable into a human body.

The heater cover 522 is a member extending along the first central axis C1 to correspond to the heater body 521, and is provided on a top surface of the heater body 521.

The heater cover 522 includes a semicircular tube accommodating groove 523 configured to surround and accommodate an upper part of the circular tube T.

The heater body 521 and the heater cover 522 are configured to cooperate with each other to 360°-surround a certain portion of the tube T.

Figure 5:
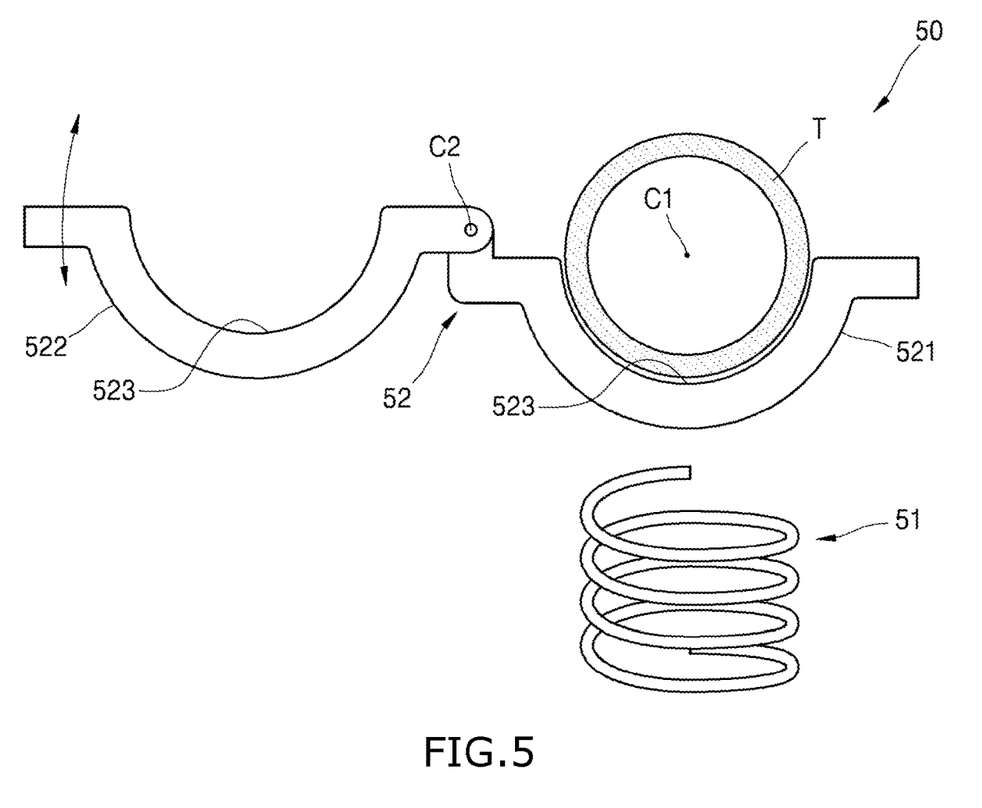
FIG. 5 is a top view illustrating that a heater cover of the heating unit illustrated in FIG. 4 is open.

The heater cover 522 is provided as a structure that is rotatable relatively to the heater body 521 about a second central axis C2 parallel with the first central axis C1 between a closed position for restraining the tube T and an open position for allowing the tube T to be taken out, as illustrated in FIG. 5.

The heater body 521 and the heater cover 522 may cooperate with each other to 360°-surround a certain portion of the tube T when the heater cover 522 is at the closed position, and the tube T may be inserted into or taken out of the tube accommodating groove 523 when the heater cover 522 is at the open position.

In the current embodiment, the pumps 11 and 21, the valves 15, 16, 17, 25, 26, and 27, the sensors 14 and 24, and the heating units 50 are automatically driven by a microcontroller unit (MCU) or the like, and are configured to accurately follow a preset medicine temperature, a dose per unit time, an injection time, etc. by feedback control.

An example of a method of using the above-described medicine injection device 100 will now be described.

Initially, one medicine pressing unit 40 is mounted on the first outlet 13 and the other medicine pressing unit 40 is mounted on the second outlet 23 as illustrated in FIG. 1.

Subsequently, one medicine container B is inserted into the medicine container holder 42 of each of the two medicine pressing units 40. In this case, the tubes T are separately equipped with the heating units 50, and the needles N are inserted into a human body.

Figure 6:
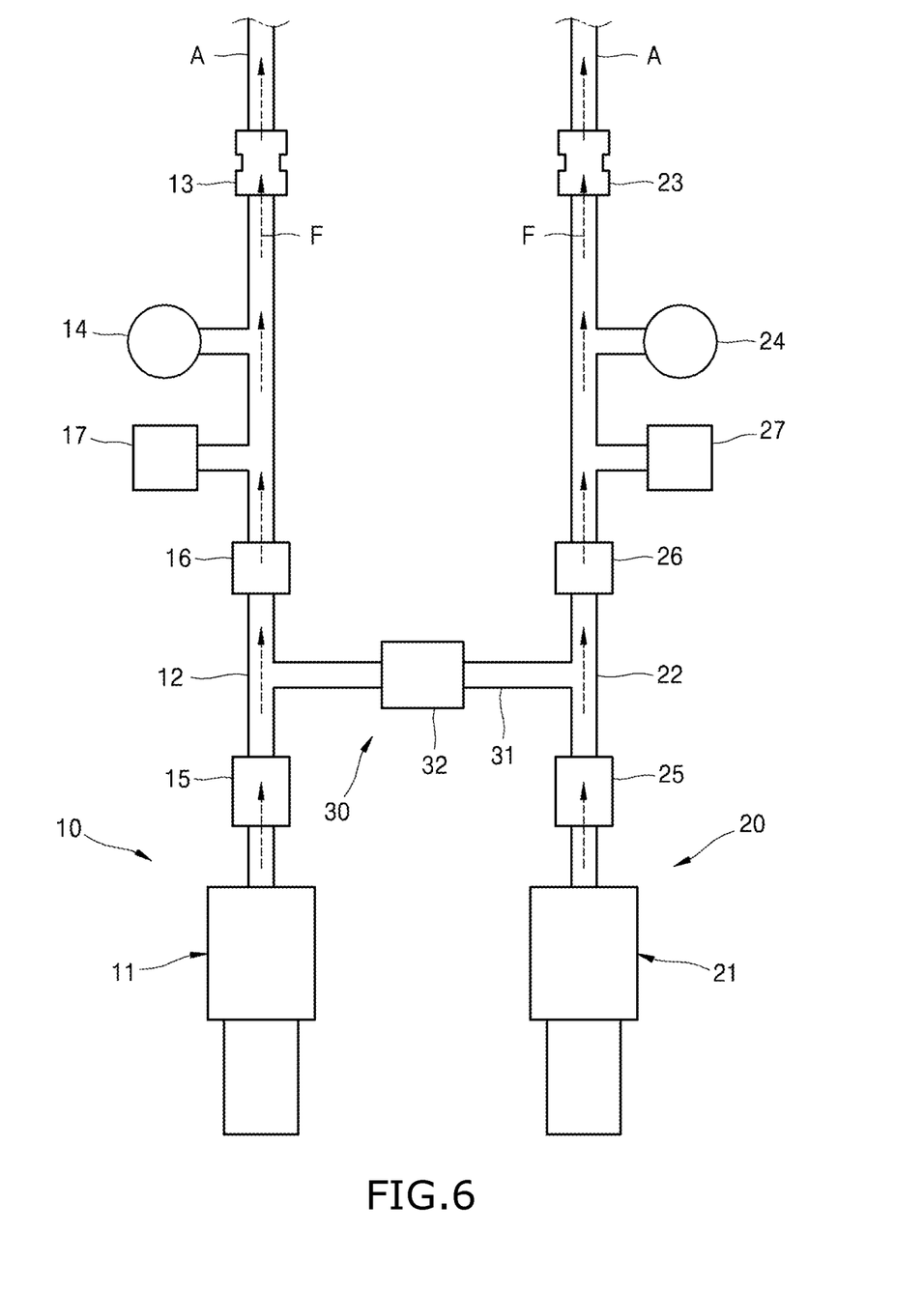
FIG. 6 is a front view illustrating that each of a first pumping unit and a second pumping unit is in charge of one of two medicine pressing units.

An air pressure desired by a user is set for each of the first and second pumping units 10 and 20, and the first and second pumps 11 and 21 are driven in such a manner that air flows F separately generated by the first and second pumps 11 and 21 proceed through the first and second pipes 12 and 22 as illustrated in FIG. 6 to inflate the inflatable parts 41 connected thereto. In this case, the first and second exhaust valves 17 and 27 and the connection pipe valve 32 are closed, and the first upstream valve 15, the first downstream valve 16, the second upstream valve 25, and the second downstream valve 26 are open.

That is, the first pumping unit 10 inflates one of the two inflatable parts 41, and the second pumping unit 20 inflates the other of the two inflatable parts 41.

When the two inflatable parts 41 inflate, the medicine containers B are pressed by the inflatable parts 41 and the medicine container holders 42 as illustrated in FIG. 3 and thus the medicine contained in the medicine containers B are injected into the human body through the tubes T and the needles N. In this case, the medicine flowing in the tubes T is heated to a preset temperature through the heating units 50.

In the current embodiment, when an air pressure sensed by the first sensor 14 is higher than a preset value, operation of the first pump 11 is temporarily stopped to block supply of air generated from the first pump 11 and, as necessary, the first exhaust valve 17 is open to reduce an internal air pressure of the inflatable part 41. Otherwise, when the air pressure sensed by the first sensor 14 is equal to or lower than the preset value, the first pump 11 may operate to increase the internal air pressure of the inflatable part 41.

While the first and second pumps 11 and 21 are operating, when the first pump 11 does not operate due to a failure or the like, the first sensor 14 senses the failure of the first pump 11 and the first upstream valve 15 is closed.

Figure 7:
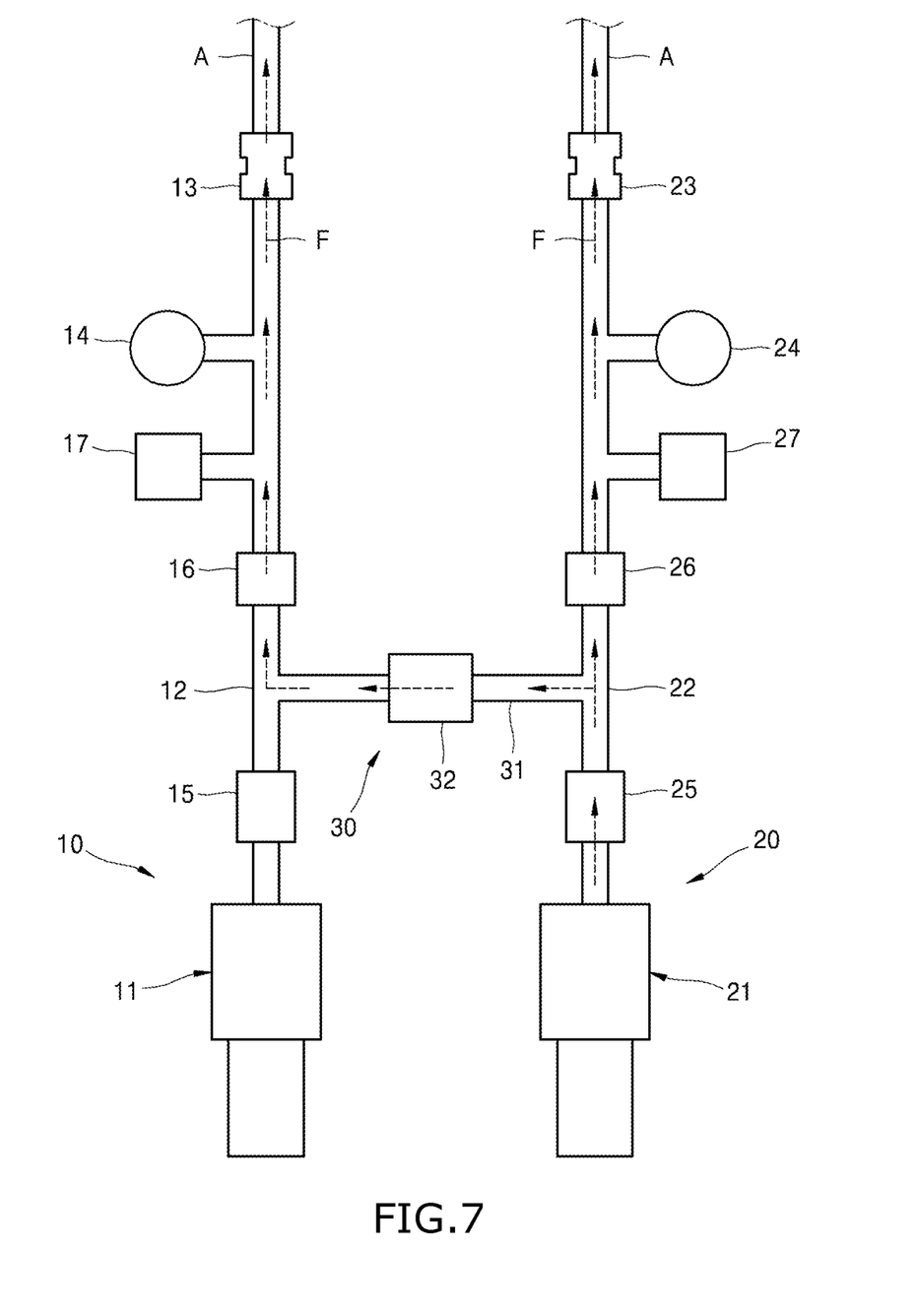
FIG. 7 is a front view illustrating that the second pump is in charge of the two medicine pressing units when the first pump does not operate.

Subsequently, the connection pipe valve 32 is open and thus the two medicine pressing units 40 are driven by the second pump 21 as illustrated in FIG. 7. This scheme may inflate one or more inflatable parts 41 connected to the first pipe 12 or/and the second pipe 22 by operating one of the first and second pumps 11 and 21 when the other of the first and second pumps 11 and 21 does not operate, and may be called a kind of fail safe operating scheme.

The above-described medicine injection device 100 is a medicine injection device capable of injecting a liquid medicine into a human body by using the medicine containers B each configured to discharge the medicine contained therein along a designated path when a pressure is applied from outside, and includes one or more medicine pressing units 40 including one or more inflatable parts 41 capable of being inflated by air to apply a pressure to the medicine container B, and the first pumping unit 10 capable of inflating one of the inflatable parts 41 by including the first pump 11 capable of generating air of a preset pressure, and the first pipe 12 connectable to the one of the inflatable parts 41. As such, a simple structure, a low rate of failure, and a low total manufacturing cost may be achieved.

The medicine injection device 100 further includes the second pumping unit 20 capable of inflating one of the inflatable parts 41 by including the second pump 21 capable of generating air of a preset pressure, and the second pipe 22 connectable to the one of the inflatable parts 41. As such, two medicine pressing units 40 may simultaneously operate.

The medicine injection device 100 further includes the connection unit 30 including the connection pipe 31 for interconnecting the first and second pipes 12 and 22, and the connection pipe valve 32 capable of opening or closing the connection pipe 31, and one or more inflatable parts 41 connected to the first and second pipes 12 and 22 may be inflated by operating one of the first and second pumps 11 and 21 when the other of the first and second pumps 11 and 21 does not operate. As such, a fail safe operating scheme may be implemented in such a manner that the two medicine pressing units 40 may operate separately even when one of the first and second pumps 11 and 21 is broken down.

The medicine injection device 100 further includes the first upstream valve 15 provided at an upstream side of the first pipe 12, the first downstream valve 16 provided at a downstream side of the first pipe 12, the second upstream valve 25 provided at an upstream side of the second pipe 22, and the second downstream valve 26 provided at a downstream side of the second pipe 22, and the connection pipe 31 has one end connected to the first pipe 12 between the first upstream valve 15 and the first downstream valve 16, and the other end connected to the second pipe 22 between the second upstream valve 25 and the second downstream valve 26. As such, a fail safe operating scheme may be implemented in a simple structure at a low cost in such a manner that one of the first and second pumps 11 and 21 may operate in an emergency when the other of the first and second pumps 11 and 21 is broken down.

The medicine injection device 100 further includes the heating units 50 for heating the medicine discharged from the medicine containers B, within a preset temperature range. As such, the medicine may be heated to an appropriate temperature and shortly thereafter be injected into the human body.

In the medicine injection device 100, the heating unit 50 operates in an IH manner by including the magnetic field generator 51 for generating a magnetic field and the heater 52 heated by a current induced by the magnetic field. As such, the medicine may be safely heated to an accurate temperature without thermal damage of other components.

In the medicine injection device 100, the heater 52 is configured to surround the tube T which is connected to the medicine container B and in which the medicine flows. As such, the medicine flowing in the tube T may be hygienically heated while the medicine is in the tube T.

In the medicine injection device 100, the medicine containers B may have a shape of a flexible bag. As such, the medicine container B itself sold in the market may be conveniently and hygienically inserted into and used in the medicine container holder 42 of the medicine pressing unit 40.

Although a pair of the medicine pressing units 40 are separately connected to the first and second pumping units 10 and 20 in the afore-described embodiments, only one medicine pressing unit 40 may be connected to the first pumping unit 10.

Although an internal air pressure of the inflatable part 41 is controlled by temporarily stopping operation of the first or second pump 11 or 21 or by temporarily opening the first or second exhaust valve 17 or 27 in the afore-described embodiments, the internal air pressure of the inflatable part 41 may also be controlled by temporarily closing or opening the first downstream valve 16 or the first upstream valve 15 or temporarily opening the first or second exhaust valve 17 or 27.

While the present invention has been particularly shown and described with reference to embodiments thereof, it will be understood by one of ordinary skill in the art that various changes in form and details may be made therein without departing from the spirit and scope of the present invention as defined by the following claims.

The invention claimed is:

1. A medicine injection device capable of injecting a liquid medicine into a human body by using a medicine container configured to discharge the medicine contained therein along a designated path when a pressure is applied from outside, the medicine injection device comprising:
   one or more medicine pressing units comprising one or more inflatable parts capable of being inflated by air to apply a pressure to the medicine container;
   a first pumping unit capable of inflating one of the inflatable parts by comprising a first pump capable of generating air of a preset pressure, and a first pipe connectable to the one of the inflatable parts;
   a second pumping unit capable of inflating one of the inflatable parts by comprising a second pump capable of generating air of a preset pressure, and a second pipe connectable to the one of the inflatable parts; and
   a connection unit comprising a connection pipe for interconnecting the first and second pipes, and a connection pipe valve capable of opening or closing the connection pipe,
   wherein one or more inflatable parts connected to the first and second pipes are inflated by operating one of the first and second pumps when another of the first and second pumps does not operate.

2. The medicine injection device of claim 1, further comprising:
   a first upstream valve provided at an upstream side of the first pipe;
   a first downstream valve provided at a downstream side of the first pipe;
   a second upstream valve provided at an upstream side of the second pipe; and
   a second downstream valve provided at a downstream side of the second pipe,
   wherein the connection pipe has one end connected to the first pipe between the first upstream valve and the first downstream valve, and another end connected to the second pipe between the second upstream valve and the second downstream valve.

3. The medicine injection device of claim 1, further comprising a heating unit for heating the medicine discharged from the medicine container, within a preset temperature range.

4. The medicine injection device of claim 3, wherein the heating unit comprises a magnetic field generator for generating a magnetic field, and a heater heated by a current induced by the magnetic field, to operate based on induction heating (IH).

5. The medicine injection device of claim 4, wherein the heater is configured to surround a tube which is connected to the medicine container and in which the medicine flows.

6. The medicine injection device of claim 1, wherein the medicine container has a shape of a flexible bag.

* * * * *